United States Patent [19]

David

[11] 4,092,741

[45] June 6, 1978

[54] PROSTHETIC DEVICE FOR USE AS A HIP JOINT

[75] Inventor: Thomas David, Vienna, Austria

[73] Assignee: Firma Ludwig Bertram GmbH & Co. KG, Hannover, Germany

[21] Appl. No.: 821,174

[22] Filed: Aug. 2, 1977

Related U.S. Application Data

[62] Division of Ser. No. 699,841, Jun. 25, 1976, abandoned.

[30] Foreign Application Priority Data

Jun. 26, 1975  Austria .................................. 4941/75

[51] Int. Cl.² ............................................. A61F 1/24
[52] U.S. Cl. ...................................... 3/1.913; 3/1.912; 128/92 C; 128/92 CA
[58] Field of Search ...................... 3/1.912; 3/1.913; 3/1.91; 1.9; 128/92 CA, 92 C

[56] References Cited

U.S. PATENT DOCUMENTS

| 2,765,787 | 10/1956 | Pellet | 128/92 CA |
| 3,067,740 | 12/1962 | Haboush | 128/92 CA |
| 3,893,196 | 7/1975 | Hochman | 3/1.913 X |

FOREIGN PATENT DOCUMENTS

| 1,047,640 | 7/1953 | France | 128/92 C |

OTHER PUBLICATIONS

McBride Type (Door Knob) Hip, Advertisement Page 4 by Austenal Labs, Inc., The Journal of Bone & Joint Surgery, Jan. 1952.

*Primary Examiner*—Ronald L. Frinks
*Attorney, Agent, or Firm*—Larson, Taylor and Hinds

[57] ABSTRACT

A prosthetic device for use as a hip joint comprises a substantially spherical portion locatable in the acetubular fossa of a pelvis bone, and a longitudinal portion locatable in a thighbone. The spherical portion is anchored within the fossa by a holding member which is fixed to the fossa.

3 Claims, 3 Drawing Figures

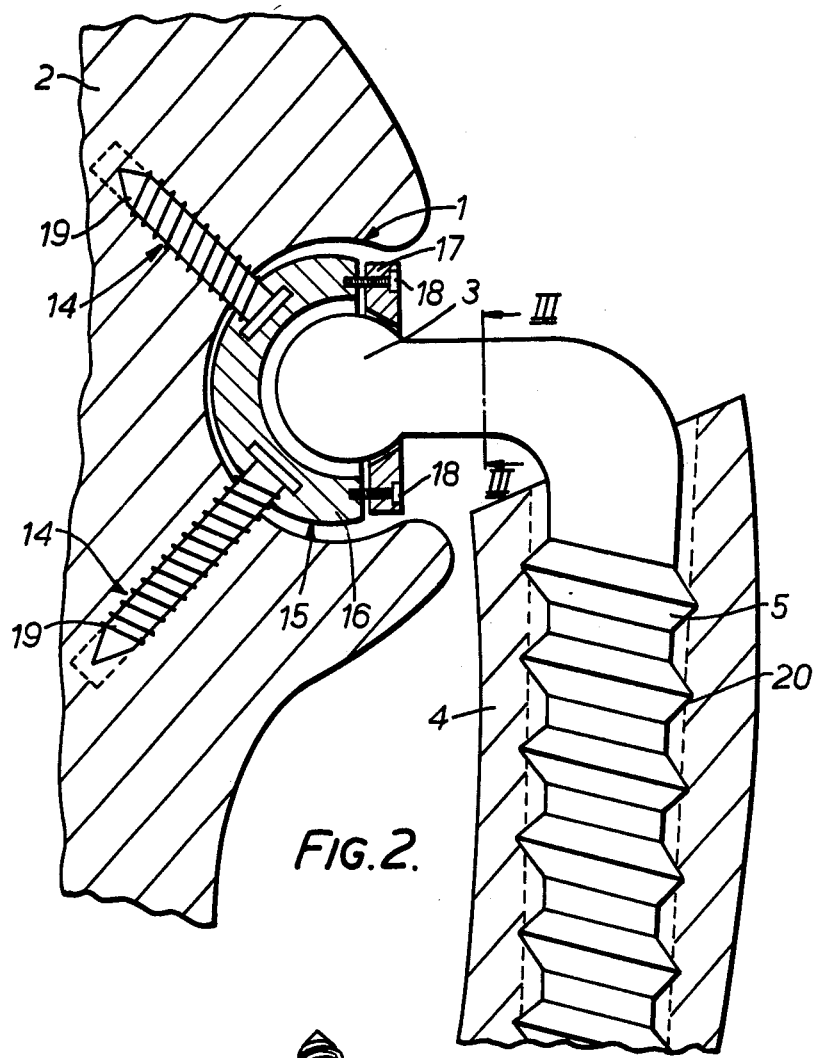
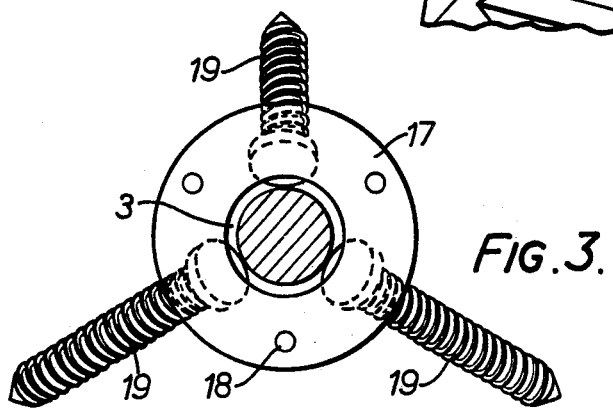
FIG.2.
FIG.3.

PROSTHETIC DEVICE FOR USE AS A HIP JOINT

This is a division of application Ser. No. 699,841, filed June 25, 1976, now abandoned.

BACKGROUND OF THE INVENTION

1. Field of the Invention.

The invention relates to a prosthetic device for use as a hip joint.

2. Description of the prior art.

There has been proposed a prosthetic device for use as a hip joint comprising a substantially spherical portion anchorable in the acetabular fossa of a pelvis bone, and an elongate portion, anchorable in a thighbone, and which is directed at an angle towards the substantially spherical portion.

To insert such a prosthetic device it is necessary to fit and anchor an artificial fossa in the pelvis bone, in an area of this bone which is very thin-walled. For this purpose, it is necessary, in the course of laborious surgical work, to produce a rear-cut recess in the pelvis bone, and this is impeded to a large extent by the muscular tissue which is particularly strong in this area. For this reason also, it is difficult and laborious to produce a reliable anchorage of the device on the pelvis bone.

SUMMARY OF THE INVENTION

According to the present invention, there is provided a prosthetic device for use as a hip joint, said device comprising a substantially spherical portion engageable in the acetabular fossa of a pelvis bone, a longitudinal portion anchorable in a thighbone, and inclined with respect to said substantially spherical portion, and at least one holding member locatable in the pelvis bone for anchoring the spherical portion in the fossa.

The manipulations which are necessary for the actual fitting of the device, and which have to be carried out from the outside of the pelvis bone, are optimally simplified, as a result of which the fixing of a suitable holding member can be carried out advantageously from the inside of the pelvis bone which is relatively accessible and is not hindered by the muscular tissue of the thigh and the hip.

In one preferred embodiment of the invention, the holding member is inserted from the side situated opposite the fossa, and therefore from the inside of the pelvis bone, into a hole which passes through the pelvis bone and which is made beforehand; the holding member can, for this purpose, have a shaft which extends through the hole and a fixing head which engages the internal side of the pelvis bone, that is the side opposite the fossa.

The device can be fixed in any desired manner to the shaft. Advantageously, the shaft of the holding member has a threaded hole onto which it is possible to screw an externally threaded shaft of a preferably metallic fixing member forming part of the substantially spherical portion of the device which consists substantially of an elastic material. Since the device consists substantially of an elastic material, the possibility is afforded of inserting the device and fixing it in the pelvis bone in a particularly simple manner as will now be described.

After an operation has exposed the fossa of the pelvis bone, first of all at least one hole is formed through the pelvis bone, for example by drilling. The shaft of the holding member is introduced into this hole, from the inside of the pelvis bone opposite the fossa until the fixing head lies on the pelvis bone. Then the shaft of the fixing member of the spherical portion of the device is screwed into the threaded hole of the shaft of the fixing member; during this stage the longitudinally-extending portion of the device is resiliently deformed to such an extent that it extends substantially along the axial direction of the threaded hole, and can be used as a grip during screwing. Then the longitudinally-extending portion of the device is introduced axially into a recess prepared in the thighbone and is anchored therein by subsequent growth of the surrounding tissue.

In another preferred embodiment of the invention, the substantially spherical portion of the prosthetic device consists of metal or other rigid material, pivotally mounted in a housing fixed by at least one holding member, which housing comprises a support portion in the form of a part-spherical cup and a closure portion forming a cover for the cup. This housing is fixed for example in the fossa of the pelvis bone by means of several screws or similar fixing members, sunk in, and preferably extending substantially radially from the cup. Since the device consists not of an elastic material but of a rigid material, the method of inserting this device is also different as will now be described.

After an operation has exposed the fossa of the pelvis bone, at least one hole is formed in the pelvis bone for example by drilling. By means of a screw or like holding member located in this hole from the outside of the pelvis bone, and embedded into the support portion, the support portion of the housing is fixed in the fossa. The spherical portion of the device is then inserted into the cup, the longitudinally-extending portion of the device having been screwed in beforehand into the thighbone after the closure portion of the housing has been pushed onto the longitudinally-extending portion. Finally the closure portion is secured on the supporting portion to hold the spherical portion in the housing.

This alternative embodiment is rather more complicated to install than the first embodiment and will normally be used only in cases in which the stresses imposed on the device are such that a device formed mainly of plastics material would be liable to deformation during use.

BRIEF DESCRIPTION OF THE DRAWINGS

The embodiments of the invention will now be further described, by way of example only with reference to the accompanying diagrammatic drawings, in which:

FIG. 2 is a section through the second embodiment of the of the device, the device being composed of metal or other rigid material; and FIG. 3 is a section taken on line III—III of FIG. 2.

DESCRIPTION OF THE PREFERRED EMBODIMENTS

Figure 1:
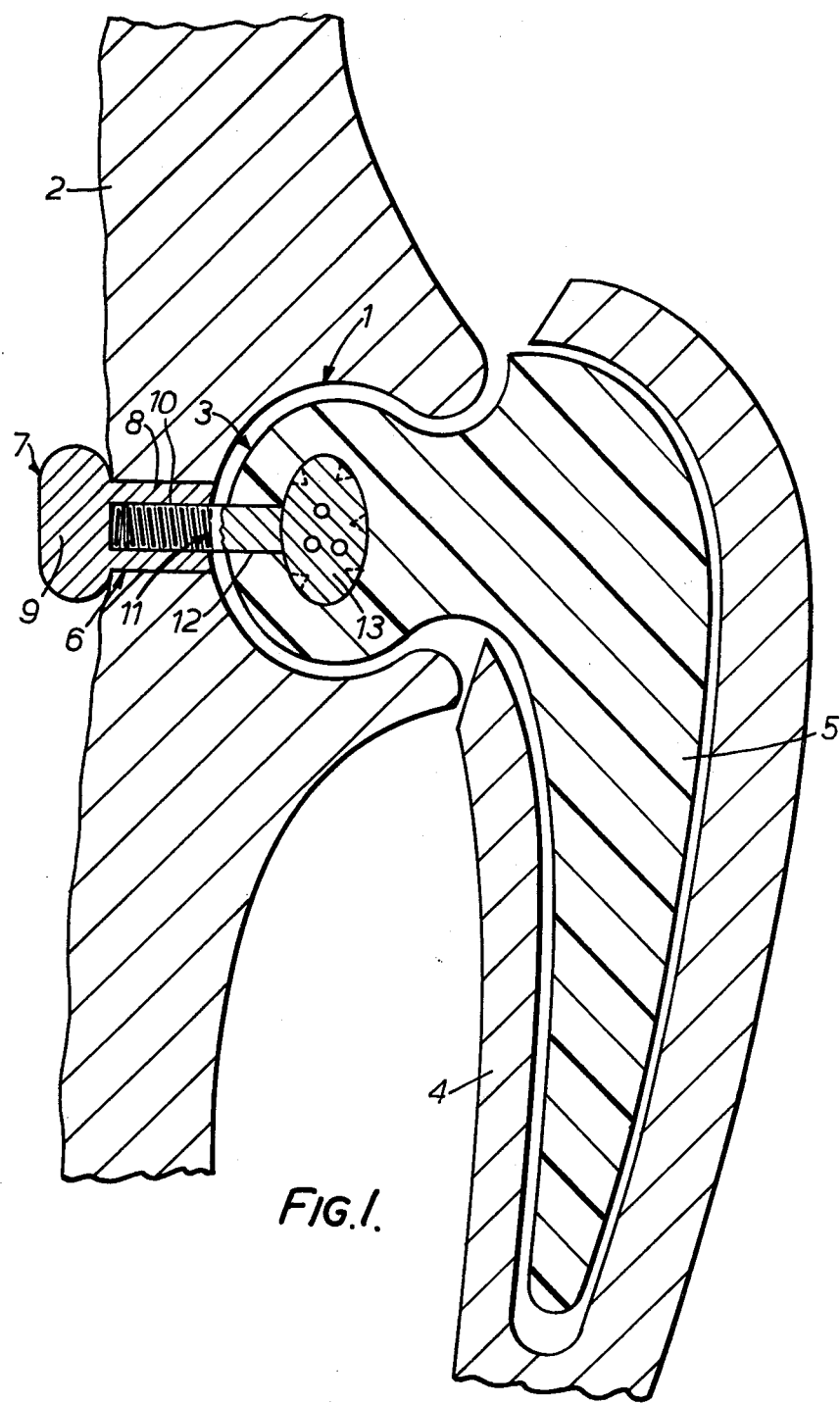
FIG. 1 is a section through the first embodiment of the prosthetic device, the device being composed substantially of elastic plastic material.

The prosthetic device shown in FIG. 1 comprises a substantially spherical portion 3 fixed in the fossa 1 of a pelvis bone 2, and a longitudinally-extending shank portion 5, which is pivotable as a result of the elasticity of the plastic material and which is fixed in a thighbone 4. The prosthetic device is a substantially one-piece construction composed of a biologically compatible plastics material of composition known per se, for example a medicinal silicone of the hard type. The spherical portion 3 is fixed to a holding member 7 passing through a hole 6 in the pelvis bone 2, the member 7 being introduced into the hole 6 from the side opposite the fossa 1, and therefore from the inside of the pelvis bone 2. For this purpose the holding member 7 has a shaft 8 which is inserted into the hole 6, and which is provided with a fixing head 9 applied against the inside of the pelvis bone 2.

The shaft 8 of the holding member 7 has a threaded hole 10 in which is screwed a shaft 12, provided with an external thread 11, of a preferably metallic fixing member 13 of the spherical portion 3. This metallic fixing member 13 is embedded in the plastics material forming the spherical portion 3 of the device, preferably by casting the plastics material of the portion 3 around the fixing member 13. The fixing member is preferably provided with notches or other formations on its surface to improve the anchorage between the fixing member and the plastics material of the spherical portions. The spherical portion 3 of the device is supported in the fossa 1 of the pelvis bone 2 with a play of about 1 to 2 mm.

The insertion of this prosthetic device has been described above. The longitudinally-extending portion 5 can be deformed and pivoted to such an extent that it can be used as a grip for screwing the shaft 12 into the threaded hole 10 of the shaft 8. In this way the insertion of the device is very simple and is not impeded to any great degree by the presence of the muscular tissue above the thighbone.

The zone of connection between the spherical portion 3 and of the longitudinally-extending portion 5 is subject to relatively high stresses and may suffer — when the stresses are pronounced — an elastic deformation, although this may only be slight. If it is absolutely necessary to prevent this alteration of shape, the prosthetic device can be made of a rigid material, for example metal, as shown in FIGS. 2 and 3.

In this embodiment, the substantially spherical portion 3 of the device is preferably made of metal or similar rigid material, and anchored in the fossa 1 of the pelvis bone 2, is rotatably mounted in a housing 15, preferably composed of plastics or the like. The housing 15 comprises a support 16 in the form of a part-spherical cup and a closure portion 17 forming a cover for the cup. The closure portion 17 is fixed by means of screws 18 or other removable securing means distributed at regular intervals around the periphery of the closure portion 17 and engaged with the support portion 16.

The housing 15 is fixed in the fossa 1 of the pelvis bone 2 by holding members 14 in the form of screws 19 or other suitable securing means, extending substantially radially with respect to the support portion 16, and embedded in the inner wall of the support portion 16.

The longitudinally-extended portion 5 of the device has a thread 20 and is axially screwed in the thighbone 4, while the threads slightly engage into the compacta of this bone which gradually grows around the thread 20 whereby the portion 5 is rigidly anchored. The method of insertion of this prosthetic device has also been already described in detail above.

The prosthetic device may be formed from materials other than those particularly described and the shape and configuration of the various parts may be different from that shown, for example the fixing member embedded in the plastics material of the spherical portion 3 may have any regular or irregular profile.

I claim:

1. A hip joint prosthesis comprising a substantially spherical portion capable of being anchored in the acetubular fossa of a pelvic bone, a shank portion capable of being anchored in a femur, the spherical portion and the shank portion being integral and being composed of an elastic material, fixing means associated with the spherical portion, and at least one holding member co-operable with the fixing means to anchor the spherical portion in the fossa, said holding member being anchorable in the pelvic bone by being inserted into a hole, previously made through the pelvic bone, from the side opposite the fossa and said holding member comprising a shaft for insertion into the hole in the pelvic bone, and a fixing head on the shaft engageable against the side of the pelvic bone opposite the fossa, the shaft of the holding member having a threaded hole and the fixing means comprising a fixing element having a threaded shaft extending from the spherical portion and engageable in the threaded hole.

2. A prosthesis according to claim 1, wherein the fixing element has an anchoring portion and the flexible material forming the spherical portion of the prosthesis is cast around the anchoring portion of the fixing element whereby to anchor the fixing element to the spherical portion.

3. A prosthesis according to claim 2, wherein the flexible material is a plastics material and the fixing element is a metal element.

* * * * *